United States Patent
Bukowick

[11] 4,002,649
[45] Jan. 11, 1977

[54] 2-FURALDOXIMINYL ALLOPHANATES

[75] Inventor: Peter A. Bukowick, Louisiana, Mo.

[73] Assignee: Hercules Incorporated, Wilmington, Del.

[22] Filed: Nov. 4, 1975

[21] Appl. No.: 628,630

Related U.S. Application Data

[63] Continuation-in-part of Ser. No. 350,218, April 11, 1973, Pat. No. 3,957,867.

[52] U.S. Cl. .............................. 260/347.3; 71/88; 260/347.2
[51] Int. Cl.² ...................................... C07D 307/54
[58] Field of Search ...................... 260/347.2, 347.3

[56] References Cited

UNITED STATES PATENTS 3,836,582   9/1974   Perronnet et al. .............. 260/347.3

Primary Examiner—Natalie Trousof
Assistant Examiner—Bernard Dentz
Attorney, Agent, or Firm—George H. Hopkins

[57] ABSTRACT

Disclosed are novel compounds of the formula

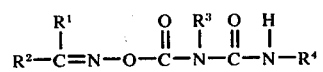

in which when $R^1$ and $R^2$ are taken separately, $R^1$ is selected independently from the group consisting of hydrogen and $C_1$–$C_7$ alkyl and $R^2$ is 2-furanyl; $R^3$ is selected from the group consisting of $C_1$–$C_7$ alkyl, allyl, phenyl, 3-halophenyl and 3,4-dihalophenyl; and $R^4$ is selected from the group consisting of $C_1$–$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl. These compounds have herbicidal activity.

2 Claims, No Drawings

2-FURALDOXIMINYL ALLOPHANATES

The application is a continuation-in-part of the U.S. patent application, Ser. No. 350,218, filed Apr. 11, 1973 now U.S. Pat. No. 397,867.

This invention is in the chemical arts. It relates to that part of organic chemistry having to do with allophanates. It also relates to herbicides.

The allophanates of this invention are oximinyl allophanates. They are represented by the general structural formula:

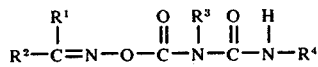

in which when $R^1$ and $R^2$ are taken separately, $R^1$ is selected independently from the group consisting of hydrogen and $C_1$–$C_7$ alkyl and $R^2$ is 2-furanyl; $R^3$ is selected from the group consisting of $C_1$–$C_7$ alkyl, allyl, phenyl, 3-halophenyl and 3,4-dihalophenyl; and $R^4$ is selected from the group consisting of $C_1$–$C_7$ alkyl, allyl, cyclohexyl, phenyl, halophenyl, tolyl, anisolyl, nitrophenyl, 3,4dihalophenyl, 1-naphthyl, p-toluenesulfonyl, trihalomethylphenyl and 2,6-dinitro-4-trihalomethylphenyl. Examples of $C_1$–$C_7$ alkyl include methyl, ethyl, propyl, isopropyl, butyl, sec. butyl, t-butyl and the like. Examples of $C_3$–$C_8$ cycloalkyl include cyclopropyl, cyclobutyl, cyclopentyl, cyclohexyl and the like. Examples of specific compounds of this invention include:

2-Furaldoximinyl-2,4-dimethyl allophanate
2-Furaldoximinyl-2-methyl-4-ethyl allophanate
2-Furaldoximinyl-2-methyl-4-allyl allophanate
2-Furaldoximinyl-2-methyl-4-(n-propyl)allophanate
2-Furaldoximinyl-2-methyl-4-(n-butyl)allophanate
2-Furaldoximinyl-2-methyl-4-phenyl allophanate
2-Furaldoximinyl-2-methyl-4-(3-chlorophenyl)allophanate
2-Furaldoximinyl-2-methyl-4-(4-chlorophenyl)allophanate
2-Furaldoximinyl-2-methyl-4-(4-methoxyphenyl)allophanate
2-Furaldoximinyl-2-methyl-4-(4-methylphenyl)allophanate
2-Furaldoximinyl-2-phenyl-4-ethyl allophanate
2-Furaldoximinyl-2-phenyl-4-allyl allophanate
2-Furaldoximinyl-2,4-diphenyl allophanate
2-Furaldoximinyl-2-phenyl-4-(3-chlorophenyl)allophanate
2-Furaldoximinyl-2-phenyl-4-(4-chlorophenyl)allophanate
2-Furaldoximinyl-2-(3-chlorophenyl)-4-methyl allophanate
2-Furaldoximinyl-2-(3-chlorophenyl)-4-ethyl allophanate
2-Furaldoximinyl-2-(3-chlorophenyl)-4-allyl allophanate
2-Furaldoximinyl-2-(3-chlorophenyl)-4-phenyl allophanate
2-Furaldoximinyl-2,4-bis-(3-chlorophenyl)allophanate
2-Furaldoximinyl-2-(3-chlorophenyl)-4-(4-chlorophenyl)allophanate Each oximinyl allophanate of this invention is made by reacting an oximinyl carbamate of the formula

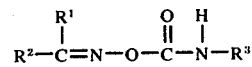

with an isocyanate of the formula $R^4N=C=O$. Reaction is effected with a catalyst such as, for example, lead naphthenate, cobalt naphthenate, and the like. Preferably, the reaction is effected in an inert liquid reaction medium such as, for example, benzene, dioxane, acetonitrile, acetone, dimethylformamide and other inert solvents. The reaction temperature is from about 25° to about 110° C., preferably in the range of from about 55° to about 100° C.

The precurser oxime carbamate for the oximinyl allophanates of this invention is made by carbamoylating an oxime of the formula

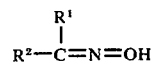

with an isocyanate of the formula $R^3N=C=O$ in the presence of a basic catalyst such as, for example, triethylamine.

Each oximinyl allophanate of this invention is also made by reacting a urea compound with phosgene to produce an allophanyl chloride and then displacing the labile chloride of the allophanyl chloride by reaction with an oxime. The reactions are represented by the following equations:

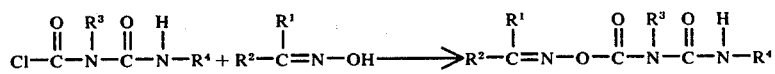

The initial step of the reaction, i.e., the reaction of the urea compound with phosgene, preferably is carried out at atmospheric pressure in an inert liquid reaction medium such as, for example, benzene. No catalyst is necessary. The reaction temperature is in the range of from about 0° C. to about 100° C.

The displacement of the labile chloride of the allophanyl chloride with an oxime takes place preferably in an inert liquid reaction medium such as, for example, benzene and toluene. A sequestering agent can be present to remove the hydrogen chloride and force the reaction to completion. Examples of such sequestering agents are tertiary amines such as, for example, triethylamine. The reaction temperature for this step is preferably between about 25° and about 80° C.

The oximinyl allophanates of this invention in general are viscous liquids at 20°–25° C., although some are crystalline solids at this temperature. In general, the water-solubility of each is less than one gram per liter of water, the acetonesolubility of each is greater than 5 grams per liter of acetone, and the benzene-solubility is greater than 10 grams per liter of benzene.

In general, they are biologically active, being phytotoxic to plants, particularly weeds. Hence, they are useful as herbicides. For herbicidal use, generally the oximinyl allophanates are incorporated into herbicidal compositions.

The herbicidal compositions of this invention comprise an effective quantity of phytotoxic material and application aid material.

The phytotoxic material comprises an oximinyl allophanate of this invention, a mixture of two or more of these oximinyl allophanates or a mixture of at least one of these oximinyl allophanates and another phytotoxic substance.

The application aid material is inert material that facilitates distribution or dispersion of the phytotoxic material. Examples of application aid material include diluents, carriers, extenders, surfactants, spreading agents, sticking agents, wind drift control agents, and the like.

The oximinyl allophanates of this invention can be used in herbicidal compositions dissolved or dispersed in a suitable liquid application aid. The liquid application aid is an inert preferably volatile solvent for the oximinyl allophanate. Watersoluble oximinyl allophanates can be dissolved in water for herbicidal use. Water-insoluble oximinyl allophanates can be dissolved in a suitable solvent, such as, for example, isophorone, cyclohexanone, methyl isobutyl ketone, xylene, and the like, to form herbicidal compositions. The solution of the oximinyl allophanate in the solvent is initially in the form of a concentrate. The concentrate can be used directly as the herbicidal composition or it can be diluted with additional solvent or it can be dispersed in water.

Solutions of the oximinyl allophanates dissolved in suitable solvents and oximinyl allophanates which are themselves liquid can also be impregnated into an inert granular solid carrier to provide solid herbicidal compositions. Examples of the inert granular carrier include attaclay, corn cobs, vermiculite, walnut hulls, and almost any granular mineral or organic material of desired particle size.

The solid oximinyl allophanates of this invention can be used in herbicidal compositions along with a finely divided inert solid application aid.

The solid oximinyl allophanates can be coated onto a granular inert carrier which has been admixed with an adhesive or sticker, such as, for example, water, oils, alcohols, glycols, aqueous gums, waxes, and the like, to form a wettable powder or ground powder. Examples of inert granular carriers include attaclay, corn cobs, vermiculite, walnut hulls and almost any other granular mineral or organic material of desired particle size.

The oximinyl allophanates of this invention can be employed according to other known methods of herbicidal application.

The best mode now contemplated of carrying out this invention is illustrated by the following working example of various aspects of this invention, including specific embodiments. This invention is not limited to these specific embodiments. In this example, unless otherwise expressly indicated, all percentages are by weight, all parts by weight are represented by w, all parts by volume are represented by v and w is to v as the kilogram is to the liter.

Example

This illustrates the preparation of 2-furaldoximinyl-2,4-dimethyl allophanate by reacting 2-furaldoximine-N-methyl carbamate with methyl isocyanate.

A solution of 5.0 w of 2-furaldoximine-N-methyl carbamate, 50 v of dry acetone, 5.6 v of 24% lead naphthanate in mineral oil, and 2.0 w of methyl cyanate is heated at reflux for 3 hours. The resulting reaction mixture is cooled and filtered. The filtrate is concentrated, resulting in a residue of a red-brown oil. The oil, a typical quantity of which is 3.6 w, consists essentially of 2-furaldoximinyl-2,4-dimethyl allophanate.

Under similar conditions and procedure the other 2-furaldoximinyl allophanates of this invention are made.

The herbicidal activities of the oximinyl allophanates of this invention are illustrated by actual test data as summarized in the following table, which data were obtained under standard test conditions with representative oximinyl allophanates of this invention.

In each case a concentrate was made from a sample of the oximinyl allophanate by dissolving it in acetone and then adding a commercially available emulsifier which is a blend of a polyoxyethylene (20) sorbitan monooleate in which the oxyethylene content is about 20 mole per cent, with mono- and di-glycerides of fat-forming fatty acids and an antioxidant mixture consisting essentially of butylated hydroxy anisol, butylated hydroxy toluene, citric acid and propylene glycol. The liquid concentrate was then admixed with water to form an aqueous emulsion with the allophanate at the desired concentration, and the resulting emulsion was then applied in post-emergence tests.

In the post-emergence tests the seeded pots were held under moist growing conditions until the seedlings had reached the first true leaf stage and then the foliage was sprayed with the emulsion sufficiently to give a coverage of the indicated pounds per acre of product under test. After a period of time sufficient for further growth, the extent of plant injury and mortality was determined using the same grading system as above. The results are shown in the following table.

TABLE

| | | | POST-EMERGENCE ACTIVITY | | | | | | | | | |
|---|---|---|---|---|---|---|---|---|---|---|---|---|
| Compound | Rate lb./ Acre | Cotton | Sorghum | Soybeans | Barnyard Grass | Corn | Teaweed | Giant Foxtail | Pigweed | Velvet Leaf | Crabgrass | Wild Mustard | Morning Glory |
| 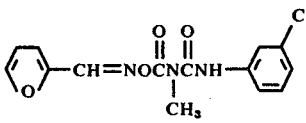 | 1 | 1 | 10 | 10 | 8 | 8 | 9 | 5 | 4 | 10 | 8 | 10 | 10 |
| | 2 | 4 | 10 | 10 | 8 | 9 | 10 | 8 | 10 | 10 | 10 | 10 | 10 |

TABLE-continued

| Compound | Rate lb./Acre | POST-EMERGENCE ACTIVITY | | | | | | | | | | | |
|---|---|---|---|---|---|---|---|---|---|---|---|---|---|
| | | Cotton | Sorghum | Soybeans | Barnyard Grass | Corn | Teaweed | Giant Foxtail | Pigweed | Velvet Leaf | Crabgrass | Wild Mustard | Morning Glory |
| (furyl)-CH=NOC(O)N(CH₃)C(O)NH-(C₆H₄)-Cl | 1 | 10 | 10 | 10 | 10 | 8 | 10 | 8 | 10 | 10 | 10 | 10 | 10 |
| | 2 | 10 | 10 | 10 | 10 | 10 | 10 | 9 | 10 | 10 | 10 | 10 | 10 |
| (furyl)-CH=NOC(O)N(3-Cl-C₆H₄)C(O)NHCH₃ | 1 | 6 | 5 | 9 | 7 | 9 | 9 | 10 | 10 | 8 | 10 | 10 | 10 |
| | 2 | 7 | 8 | 9 | 10 | 10 | 10 | 10 | 10 | 9 | 10 | 10 | 10 |

The oximinyl allophanates of this invention exhibit higher herbicidal activity than the corresponding oximinyl carbamates.

Various features, advantages and specific embodiments of this invention will be readily apparent to those exercising ordinary skill in the art after reading the foregoing disclosures. Such specific embodiments are within the scope of the claimed subject matter unless expressly indicated otherwise. Moreover, while a specific embodiment of this invention has been described in considerable detail, variations and modifications of it can be effected without departing from the spirit and scope of the invention as disclosed and claimed.

The terminology "consisting essentially of" as used in the specification (disclosure and claims) excludes any unrecited substance at a concentration sufficient to substantially adversely affect the essential properties and characteristics of the composition being defined, while permitting the presence of one or more unrecited substances at concentrations insufficient to substantially adversely affect said essential properties and characteristics.

What I claim and desire to protect by Letters Patent is:

1. A compound having the following structural formula:

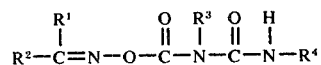

in which when $R^1$ and $R^2$ are taken separately, $R^1$ is selected independently from the group consisting of hydrogen and $C_1$–$C_7$ alkyl and $R^2$ is 2-furanyl; $R^3$ is selected from the group consisting of $C_1$–$C_7$ alkyl, allyl, phenyl, 3-halophenyl and 3,4-dihalophenyl; and $R^4$ is selected from the group consisting of $C_1$–$C_7$ alkyl, allyl, cyclohexyl, phenyl, halophenyl, tolyl, anisolyl, nitrophenyl, 3,4-dihalophenyl, 1-naphthyl, p-toluene sulfonyl, trihalomethylphenyl and 2,6-dinitro-4-trihalomethylphenyl.

2. A compound according to claim 1 in which $R^1$ is hydrogen and $R^3$ and $R^4$ are methyl.

* * * * *